US009585627B2

United States Patent
Liu et al.

(10) Patent No.: US 9,585,627 B2
(45) Date of Patent: Mar. 7, 2017

(54) HISTOLOGICAL DIFFERENTIATION GRADE PREDICTION OF HEPATOCELLULAR CARCINOMA IN COMPUTED TOMOGRAPHY IMAGES

(71) Applicant: Siemens Healthcare GmbH, Erlangen (DE)

(72) Inventors: David Liu, Franklin Park, NJ (US); Shaohua Kevin Zhou, Plainsboro, NJ (US)

(73) Assignee: SIEMENS HEALTHCARE GMBH, Erlangen (DE)

( * ) Notice: Subject to any disclaimer, the term of this patent is extended or adjusted under 35 U.S.C. 154(b) by 351 days.

(21) Appl. No.: 14/454,128

(22) Filed: Aug. 7, 2014

(65) Prior Publication Data
US 2015/0051484 A1 Feb. 19, 2015

Related U.S. Application Data

(60) Provisional application No. 61/865,728, filed on Aug. 14, 2013.

(51) Int. Cl.
*G06K 9/00* (2006.01)
*A61B 6/00* (2006.01)
(Continued)

(52) U.S. Cl.
CPC .......... *A61B 6/5217* (2013.01); *A61B 6/032* (2013.01); *A61B 6/50* (2013.01); *G06T 7/0012* (2013.01);
(Continued)

(58) Field of Classification Search
CPC ......... A61B 6/5217; A61B 6/50; A61B 6/032; G06T 7/0012; G06T 2207/10081;
(Continued)

(56) References Cited

U.S. PATENT DOCUMENTS 6,418,236 B1 * 7/2002 Ellis .................. G06K 9/00127
382/128
6,718,053 B1 * 4/2004 Ellis .................. G01N 15/1475
345/604

(Continued)

OTHER PUBLICATIONS

Aapo Hyvarinen, et al. "Natural Image Statistics—A probabilistic approach to early computational vision", Springer, Feb. 27, 2009, pp. 1-487.

(Continued)

*Primary Examiner* — John Strege

(57) ABSTRACT

A method of determining the histological grade of Hepatocellular Carcinoma (HCC) including: acquiring a Computed Tomography (CT) image of a person including an HCC tumor; delineating the HCC tumor; and assigning a histological grade to the HCC tumor, wherein assigning the histological grade to the HCC tumor includes: applying a plurality of filters to the HCC tumor, wherein each of the filters produces a corresponding response image and, for each of the filters, a convolution operation is performed on the filter and the CT image to produce the response image corresponding to that filter; computing an average response of the HCC tumor in each of the response images and recording each of the average responses as an Independent Subspace Analysis (ISA) feature; and determining the histological grade of the HCC tumor based on the ISA features by using a classifier.

21 Claims, 5 Drawing Sheets

(51) Int. Cl.
*A61B 6/03* (2006.01)
*G06T 7/00* (2006.01)

(52) U.S. Cl.
CPC ............... *G06T 2207/10081* (2013.01); *G06T 2207/20081* (2013.01); *G06T 2207/30056* (2013.01); *G06T 2207/30096* (2013.01)

(58) Field of Classification Search
CPC . G06T 2207/30056; G06T 2207/30096; G06T 2207/20081
USPC ........................................................ 382/128
See application file for complete search history.

(56) References Cited

U.S. PATENT DOCUMENTS

| | | | | |
|---|---|---|---|---|
| 7,941,275 | B2* | 5/2011 | Gholap | G01N 33/5091 382/128 |
| 2003/0165263 | A1* | 9/2003 | Hamer | G06K 9/00127 382/133 |
| 2008/0166035 | A1* | 7/2008 | Qian | G06T 7/0012 382/133 |
| 2009/0181394 | A1* | 7/2009 | Chung | C12Q 1/6886 435/6.14 |
| 2011/0170759 | A1* | 7/2011 | Bjornerud | G06T 7/0012 382/131 |
| 2014/0314292 | A1* | 10/2014 | Kamen | A61B 6/463 382/131 |

OTHER PUBLICATIONS

Fergus Davnall et al., "Assessment of tumor heterogeneity: an emerging imaging tool for clinical practice?", Springer, Insights Imaging (2012) 3: 573-589.

Neha Bhooshan, et al., "Cancerous Breast Lesions on Dynamic Contrast-enhanced MR Images: Computerized Characterization for Image-based Prognostic Markers", Radiology, vol. 254: No. 3—Mar. 2010, pp. 680-690.

Leo Breiman, "Random Forests", Machine Learning, 45, 5-32, 2001.

Francesca Ng, et al. "Assessment of tumor heterogeneity by CT texture analysis: Can the largest cross-sectional area be used as an alternative to whole tumor analysis?" European Journal of Radiology 82 (2013) 342-348.

Vicky Goh, et al., "Assessment of Response to Tyrosine Kinase Inhibitors in Metastatic Renal Cell Cancer: CT Texture as a Predictive Biomarker", Radiology: vol. 261: No. 1—Oct. 2011, pp. 165-171.

Balaji Ganeshan, et al., "Non-Small Cell Lung Cancer: Histopathologic Correlates for Texture Parameters at CT", Radiology: vol. 266, No. 1—Jan. 2013, pp. 326-336.

Kenneth A. Miles, et al., "Colorectal Cancer: Texture Analysis of Portal Phase Hepatic CT Images as a Potential Marker of Survival", Radiology: vol. 250, No. 2—Feb. 2009, pp. 444-452.

* cited by examiner (a)      (b)      (c)      (d)      (e)

HISTOLOGICAL DIFFERENTIATION GRADE PREDICTION OF HEPATOCELLULAR CARCINOMA IN COMPUTED TOMOGRAPHY IMAGES

CROSS-REFERENCE TO RELATED APPLICATION

This application claims priority to U.S. provisional application No. 61/865,728, filed Aug. 14, 2013, the disclosure of which is incorporated by reference herein in its entirety.

TECHNICAL FIELD

The present invention relates to histological grading of Hepatocellular Carcinoma.

DISCUSSION OF THE RELATED ART

Hepatocellular Carcinoma (HCC) is the most common histological type of primary liver cancer. The HCC histological grade is one of the independent predictors of post-operative recurrence and has been used in determining therapeutic options for HCCs. Pre-operative prediction of HCC histological grade is important; it was suggested that a surgical plan could be modified depending on the histological grade, since the biologic aggressiveness of a tumor could be reflected from the degree of differentiation.

Pre-operative assessments have been limited by the risk of tumor seeding along the biopsy tract, or by a lack of reflection of the heterogeneous histology, i.e., sampling errors. Therefore, the development of a noninvasive test for assessing the tumor grade during pre-operative staging is important. Computed Tomography (CT) imaging is very common for HCC identification and tumor localization. The use of CT imaging may have even greater implications if HCC tumor grade can be predicted from CT pre-operatively and non-invasively.

SUMMARY OF THE INVENTION

According to an exemplary embodiment of the present invention, a method of determining the histological grade of Hepatocellular Carcinoma (HCC) comprises: acquiring a Computed Tomography (CT) image of a person including an HCC tumor; delineating the HCC tumor; and assigning a histological grade to the HCC tumor, wherein assigning the histological grade to the HCC tumor comprises: applying a plurality of filters to the HCC tumor, wherein each of the filters produces a corresponding response image and, for each of the filters, a convolution operation is performed on the filter and the CT image to produce the response image corresponding to that filter; computing an average response of the HCC tumor in each of the response images and recording each of the average responses as an Independent Subspace Analysis (ISA) feature; and determining the histological grade of the HCC tumor based on the ISA features by using a classifier.

The classifier includes Random Forest regression.

The histological grade of the HCC tumor includes grade-1, grade-2, or grade-3.

The histological grade of the HCC tumor is obtained pre-operatively and non-invasively.

The filters are obtained in a training stage.

The training stage comprises: subjecting a plurality of sample CT images, each image having at least one HCC tumor delineated therein, to ISA to yield the plurality of filters; applying the filters to each tumor by using the convolution operation; recording the average response per filter as an ISA feature; and using the classifier to predict the histological grade of each tumor based on its ISA features.

The HCC tumor is delineated by a medical professional.

According to an exemplary embodiment of the present invention, a system for determining the histological grade of HCC comprises: a memory device for storing a program; a processor in communication with the memory device, the processor operative with the program to: acquire a CT image of a person including an HCC tumor; delineate the HCC tumor; and assign a histological grade to the HCC tumor, wherein the processor is further operative with the program in assigning the histological grade to the HCC tumor to: apply a plurality of filters to the HCC tumor, wherein each of the filters produces a corresponding response image and, for each of the filters, a convolution operation is performed on the filter and the CT image to produce the response image corresponding to that filter; compute an average response of the HCC tumor in each of the response images and record each of the average responses as an ISA feature; and determine the histological grade of the HCC tumor based on the ISA features by using a classifier.

The classifier includes Random Forest regression.

The histological grade of the HCC tumor includes grade-1, grade-2, or grade-3.

The histological grade of the HCC tumor is obtained pre-operatively and non-invasively.

The filters are obtained in a training stage.

The processor is further operative with the program in the training stage to: subject a plurality of sample CT images, each image having at least one HCC tumor delineated therein, to ISA to yield the plurality filters; apply the filters to each tumor by using the convolution operation; record the average response per filter as an ISA feature; and use the classifier to predict the histological grade of each tumor based on its ISA features.

The HCC tumor is delineated by a medical professional.

According to an exemplary embodiment of the present invention, a computer program product for determining the histological grade of HCC comprises: a non-transitory computer readable storage medium having computer readable program code embodied therewith, the computer readable program code comprising: computer readable program code configured to perform the steps of: acquiring a CT image of a person including an HCC tumor; delineating the HCC tumor; and assigning a histological grade to the HCC tumor, wherein assigning the histological grade to the HCC tumor comprises: applying a plurality of filters to the HCC tumor, wherein each of the filters produces a corresponding response image and, for each of the filters, a convolution operation is performed on the filter and the CT image to produce the response image corresponding to that filter; computing an average response of the HCC tumor in each of the response images and recording each of the average responses as an ISA feature; and determining the histological grade of the HCC tumor based on the ISA features by using a classifier.

The classifier includes Random Forest regression.

The histological grade of the HCC tumor includes grade-1, grade-2, or grade-3.

The histological grade of the HCC tumor is obtained pre-operatively and non-invasively.

The filters are obtained in a training stage.

The training stage comprises: subjecting a plurality of sample CT images, each image having at least one HCC tumor delineated therein, to ISA to yield the plurality filters; applying the filters to each tumor by using the convolution operation; recording the average response per filter as an ISA feature; and using the classifier to predict the histological grade of each tumor based on its ISA features.

The HCC tumor is delineated by a medical professional.

DETAILED DESCRIPTION OF EXEMPLARY EMBODIMENTS

Hereinafter exemplary embodiments of the present invention will be disclosed. In an exemplary embodiment of the present invention, there is provided a method of obtaining the histological grade of Hepatocellular Carcinoma (HCC) pre-operatively and non-invasively from Computed Tomography (CT) images. Although CT images are described in the following examples, other image types obtained from other imaging modalities for example, Magnetic Resonance Imaging (MRI) and Positron Emission Tomography (PET), may be used with this invention.

Figure 1:
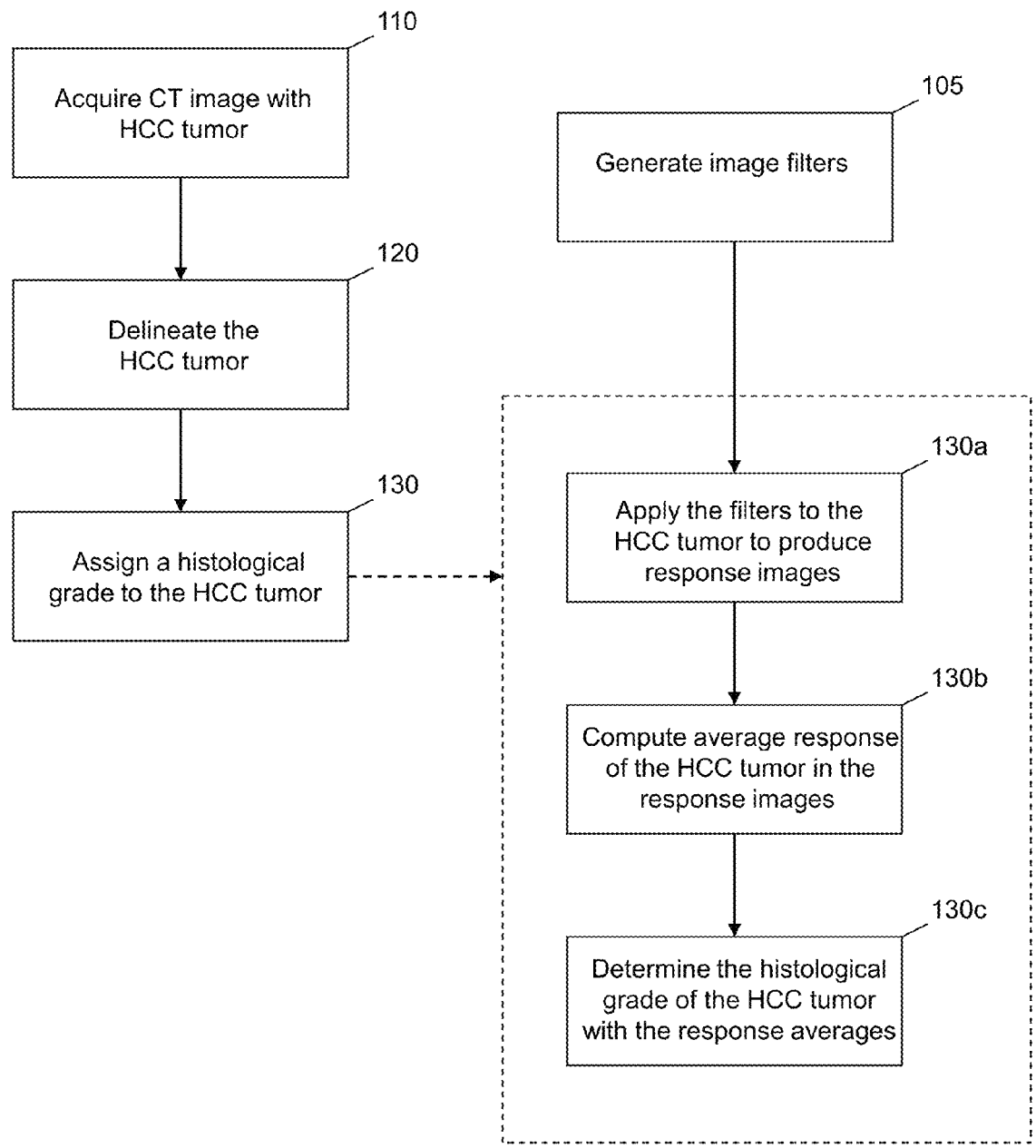
FIG. 1 is a flowchart of a method according to an exemplary embodiment of the present invention.

FIG. 1 is a flowchart of a method according to an exemplary embodiment of the present invention.

Figure 2:
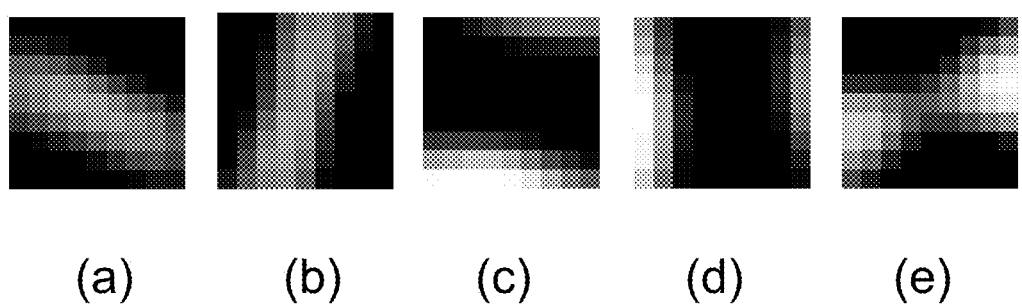
FIG. 2 shows image filters produced in a round of leave-one-out cross-validation (LOOCV), according to an exemplary embodiment of the present invention.

As shown in FIG. 1, image filters may first be generated (105). Once generated, the image filters may be stored in memory on a computer. Examples of the image filters are shown in FIG. 2. FIG. 2 will be described in greater detail later.

The image filters are generated in a training stage. As a real life example of the training stage, 91 consecutive patients who were suspected of having chronic liver disease or focal hepatic lesions underwent liver histopathology, during which tumor grade was determined. Contrast-enhanced CT was performed on 84 patients. Seven patients did not undergo CT imaging due to allergy or renal dysfunction. All imaging examinations were performed within two weeks of histopathology reports. Detailed patient statistics are shown in Table 1.

a grade-3 tumor, one female had a grade-1 and a grade-3 tumor, and one male had two grade-2 tumors.

Two pathologists (undisclosed for anonymous review) specializing in liver pathology (both with >10 years of experience) performed the histological grading of HCC based on tumor differentiation. They did this on biopsy samples in order to obtain a ground truth. Well-differentiated (grade-1), moderately-differentiated (grade-2), poorly-differentiated and undifferentiated (grade-3) types were recognized, according to the definitions proposed by the World Health Organization. When multiple tumors were present in one patient, the tumor with the highest grade was used. Detailed tumor statistics are shown in Table 1.

After obtaining the ground truth, CT imaging was performed using a Siemens 16-detector row scanner. As mentioned above, these imaging exams were performed within two weeks of the Unenhanced CT scans were obtained first; subsequently, 100 ml nonionic contrast material with a concentration of 300 mgI/ml (Ultravist®) at a rate of 3 ml/sec through an 18-gauge angiographic catheter was administered intravenously. Image acquisition in the arterial, portal venous, and delayed phases began 40, 70, and 180 seconds, respectively, after initiation of contrast medium injection.

At this time, the performance of the inventive automated tumor grading system was evaluated by leave-one-out cross-validation (round-robin-by-case), which provides an accurate estimation of the prediction performance among common cross-validation techniques. In each round of validation, all patients except one were used to build a computer program that predicts the tumor grade of the one patient that had been left out as a test sample. This process was repeated 84 times until every patient had been used once as a test sample.

The maximal likelihood-fitted binormal Receiver Operating Characteristic (ROC) curve and the Area Under ROC Curve (AUC) were used to assess the prediction accuracy of automated tumor grading. The optimal cutoff values for differentiating between tumor grades were chosen at the highest possible sensitivity and specificity (maximal Youden index, defined as sensitivity plus specificity minus 1) on the ROC curves. Multiple comparison tests across the predicted tumor grades were performed with the Kruskal-Wallis test (R statistical software version 2.15.2). For all analyses, $P<0.05$ was considered to denote a significant difference.

Still in the training stage, radiology reports were done by two radiologists (A and B, undisclosed for anonymous review), both with more than 10 years of experience, with

TABLE 1

Patient Statistics stratified by tumor grade.

| Parameter | Grade-1 | Grade-2 | Grade-3 | All |
|---|---|---|---|---|
| Age (y): mean, std. dev., (range) | 57.5 ± 6.5 (45-69) | 52.7 ± 9.8 (30-72) | 53.2 ± 9.4 (40-68) | 53.5 ± 9.3 (30-72) |
| No. of men | 10 | 41 | 21 | 72 |
| No. of women | 3 | 9 | 3 | 15 |
| Tumor area ($mm^2$): mean, median (range) | 886, 741 (268-2561) | 3645, 2103 (294-26275) | 55592, 4254 (547-18810) | 3739, 1626 (268-26275) |
| No. of HCCs | 13 | 50 | 24 | 87 |
| No. of patients with one HCC | 11 | 48 | 22 | 81 |
| No. of patients with multiple HCCs | 2 | 1 | 2 | 3 |

Referring to Table 1, the average of these 84 patients is 53.5 years old and most of them have only one tumor. Three patients have multiple tumors: one male had a grade-1 and consensus reading. The location of each lesion was documented in the reports. One radiologist (A) then delineated a region of interest around the lesion boundary in the arterial phase image. The delineation took place on the slice with maximum tumor diameter. Both radiologists were blinded to the histopathology report.

Next, a quantifier (marker) according to an exemplary embodiment of the present invention was used for HCC tumor grading. This quantifier may be referred to as the RFISA quantifier.

In this case, the delineated tumor region was first dilated (enlarged) by three pixels with software to include surrounding information. Image patches of size 9×9 pixels were extracted uniformly within the region with step size of one pixel; patches were then whitened with Principal Component Analysis (PCA) and subjected to Independent Subspace Analysis (ISA), which yielded five image filters. PCA and ISA are described by Aapo Hyvärinen, Jarmo Hurri and Patrik O. Hoyer in "Natural Image Statistics—A probabilistic approach to early computational vision," Springer, Feb. 27, 2009, the disclosure of which is incorporated by reference herein in its entirety. The five filters were applied to each tumor by the convolution operation described in "Natural Image Statistics—A probabilistic approach to early computational vision," and the average response per filter tumor was recorded as an ISA feature. We used Random Forest regression to predict the histological grade of each tumor based on its five ISA features. The regression response variable is the RFISA quantifier. Random Forest regression is described by Leo Breiman in "Random Forests," Machine Learning, 45, 5-32, 2001, the disclosure of which is incorporated by reference herein in its entirety.

As mentioned above, a total of 84 independent rounds (iterations) of leave-one-out-cross-validation (LOOCV) were performed. FIG. 2 shows the image filters (a-e) produced in one of the rounds of LOOCV as an example. Five image filters were generated in each round by ISA. Every image filter appeared "bar-like" with different orientations. We observed very similar image features every round (images not shown for the other 83 rounds).

Turning to the non-training stage, with reference to FIG. 1, a CT image of a patient with an HCC tumor is obtained (110). After the CT image is obtained, the HCC tumor is delineated (120). The CT image acquisition and the HCC tumor delineation may be performed by using the techniques described above. Once the HCC tumor is delineated, a histological grade is assigned thereto (130). The assignment of the histological grade is automated; the details of which will now be described.

Figure 3:
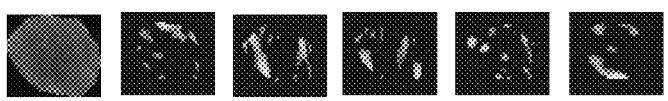
FIG. 3 illustrates three tumors of grade-1, grade-2, and grade-3, respectively, and corresponding results of convolution with five image filters in a round of LOOCV, according to an exemplary embodiment of the present invention.
Figure 3:
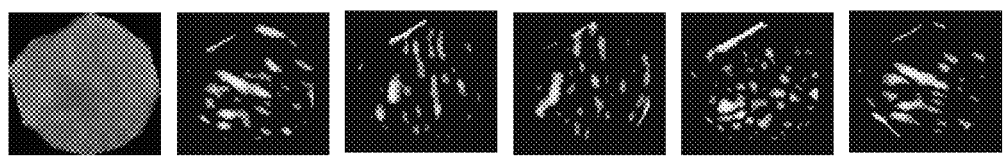
Figure 3:
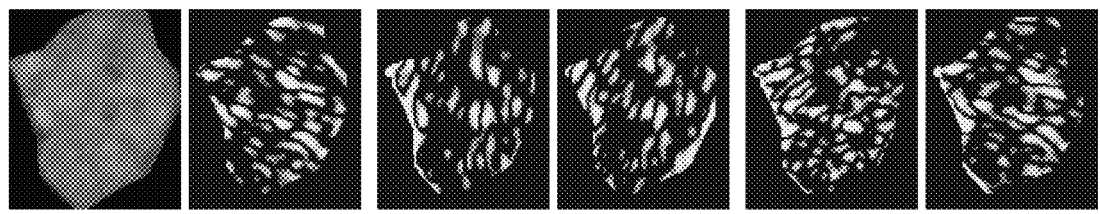

For example, as shown in FIG. 1, the previously generated image filters are applied to the delineated HCC tumor to produce response images (130a). Here, each of the filters produces a corresponding response image. For example, in FIG. 3, the five image filters of FIG. 2 produce five response images (a1-a5) for tumor (a), five response images (b1-b5) for tumor (b) and five response images (c1-c5) for tumor (c). In order to produce a response image for a respective filter, a convolution as is performed on that filter and the delineated HCC. The convolution operation may be the same as that described above. FIG. 3 illustrates three tumors of grade-1 (a), grade-2 (b), and grade-3 (c), respectively, and the corresponding results of convolution with the five image filters in one of the rounds. The areas of the grade-1, grade-2, and grade-3 tumors are 741 mm$^2$, 2103 mm$^2$, and 4254 mm$^2$, respectively.

Next, an average response of the HCC tumor in each of the five response images is computed and recorded as an ISA feature (130b). The average response may be computed as the mean intensity of images resulting from the convolution computed earlier. These five numbers are then input to the Random Forest regression to determine the histological grade of the HCC tumor (130c). As noted above, the histological grade of the HCC tumor may be grade-1, grade-2 or grade-3. Although the Random Forest regression is used as the classifier in this example, other classifiers may be used for example linear regression, logistic regression or Support Vector Machine regression.

Tumor grading was also performed by using a Homogeneity quantifier and a Tumor Size quantifier, in place of the inventive RFISA quantifier.

The Homogeneity quantifier is a classical image texture feature, with the following equation:

$$Hgt = \Sigma_{i=1}^{N_g} \Sigma_{j=1}^{N_g} P(i,j)/(1+|i-j|)$$

where P(i,j) counts the number of times a pixel with value i is adjacent to a pixel with value j and then dividing by the total number of such comparisons made. $N_g$ is the number of gray levels in the image.

The Tumor Size quantifier measured the area of the human-delineated tumor region.

Figure 4:
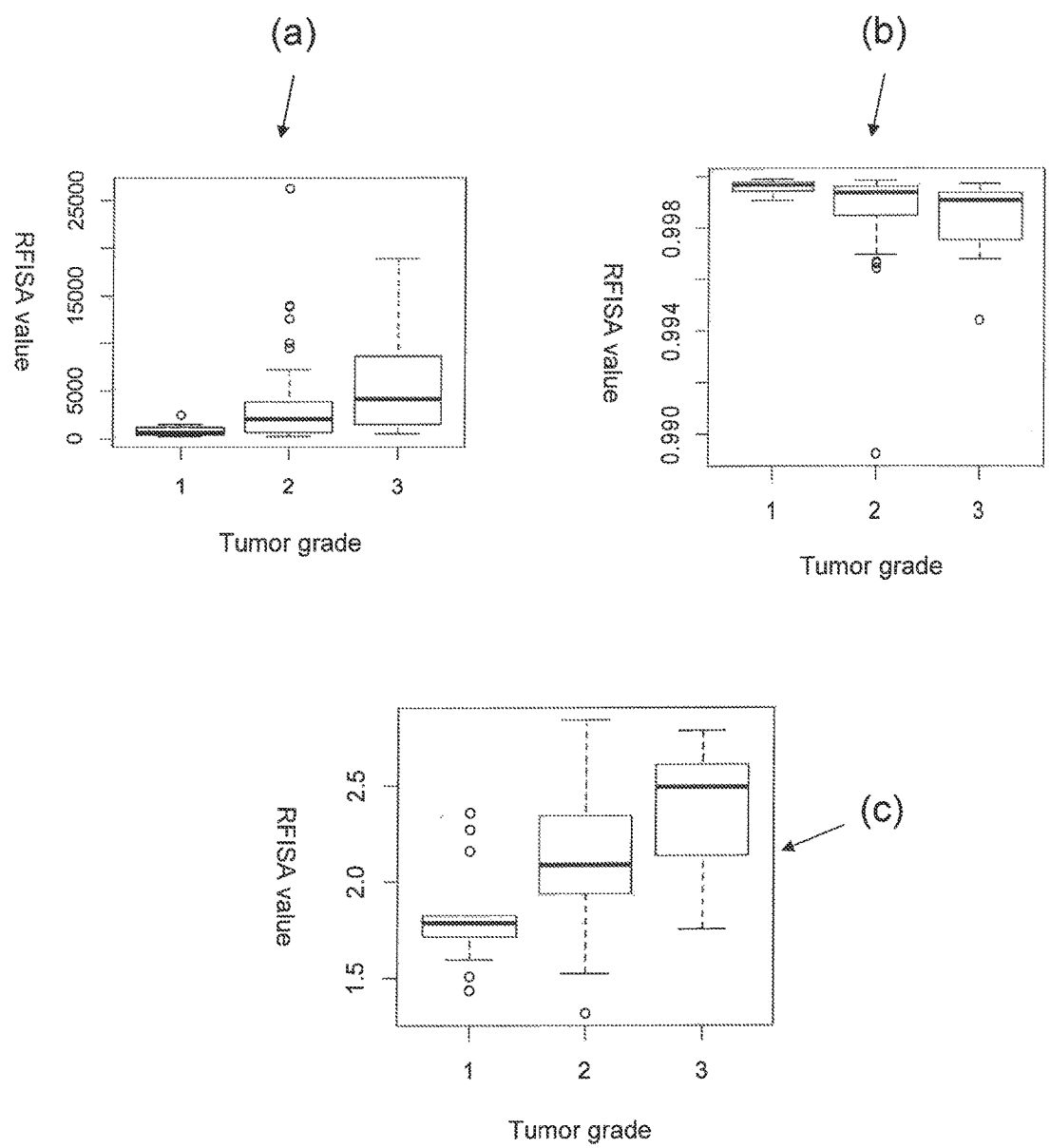
FIG. 4 shows boxplots of quantifier values versus tumor grade.

FIG. 4 shows boxplots of quantifier values versus tumor grade. For every quantifier (RFISA, Hogeneity, Tumor Size), the difference among three tumor grades was significant. Also, the quantifier values of grade-1 tumors were significantly different from higher grade tumors. Finally, the quantifier values for grade-2 tumors were significantly different from grade-3 tumors.

In particular, in (a) of FIG. 4 the boxplot of quantifier RFISA versus tumor grade is shown, in (b) of FIG. 4 the boxplot of quantifier Homogeneity versus tumor grade is shown, and in (c) of FIG. 4 the boxplot of Tumor Size versus tumor grade is shown. As mentioned above, within each boxplot, the differences were significant (Kruskal Wallis test, P<0.001). Pairwise comparisons used the Wilcoxon rank-sum test with Bonferroni correction. The lower edge of each box indicates the 25$^{th}$ percentile, and the upper edge of each box indicates the 75$^{th}$ percentile. The horizontal line in the middle of each box indicates the median. The lines extending from each box indicate the smallest and largest datum within 1.5 times the interquartile range. The horizontal axis represents tumor grade-1, grade-2, and grade-3.

In (a) of FIG. 4, the RFISA values of grade-1 tumors were significantly higher than those of grade-2 and grade-3 (P=0.008 and P<0.001, respectively). The RFISA values of grade-2 tumors were significantly higher than those of grade-3 (P=0.003).

In (b) of FIG. 4, the Homogeneity values of grade-1 tumors were significantly higher than those of grade-2 and grade-3 (P=0.008 and P<0.001, respectively). The Homogeneity values of grade-2 tumors were significantly higher than those of grade-3 (P=0.034).

In (c) of FIG. 4, grade-1 tumors have significantly smaller sizes than grade-2 and grade-3 tumors (P=0.004 and P<0.001, respectively). Grade-2 tumors have significantly smaller sizes than grade-3 tumors (P=0.041).

The Spearman rank correlation (R) of each quantifier with tumor grade is shown in Table 2, along with the corresponding P-values. RFISA showed the highest correlation with tumor grade (R=0.484), followed by Tumor Size (R=0.414) and Homogeneity (R=−0.412).

TABLE 2

Correlation of three quantifiers (RFISA, Homogeneity, Tumor Size) with tumor grade.

| Quantifier | Spearman's rank correlation with Tumor Grade | P Value |
|---|---|---|
| RFISA | 0.484 | 5.86e−06 |
| Homogeneity | −0.412 | 7.18e−05 |
| Tumor Size | 0.414 | 6.56e−05 |

The ROC analysis results are shown in Table 3 and Table 4. AUCs and its 95% confidence intervals, sensitivities, and specificities are shown. Table 3 shows the results of ROC analysis of tumor grade differentiation (grade-1 vs. grades-2&3, and grades-1&2 vs. grade-3). The RFISA quantifier distinguishes grade-1 from grades-2&3 tumors with 82% sensitivity and 77% specificity. Table 4 shows the area under ROC curve (AUC) of quantifier values in pairwise comparisons (grade-1 vs. grade-2, grade-2 vs. grade-3, and grade-1 vs. grade-3). The RFISA quantifier differentiated between grade-1 and grade-3 tumors with 96% sensitivity and 77% specificity.

TABLE 3

ROC Analysis of quantifiers for tumor grades. AUCs are cited with standard errors. Numbers in parentheses are 95% confidence intervals. Sensitivity and specificity are computed in terms of identification of the higher-grade tumors. Data in parentheses are numbers used to calculate percentages. The optimal cutoff values for differentiating between tumor grades were chosen at the highest possible sensitivity and specificity (maximal Youden index defined as sensitivity plus specificity minus 1) on the ROC curves.

| Quantifier | AUC | Sensitivity (%) | Specificity (%) |
|---|---|---|---|
| | Differentiation between Grade 1 versus Grade 2-3 Tumors | | |
| RFISA | 0.81 ± 0.06 (0.66, 0.91) | 82 (61/74) | 77 (10/13) |
| Homogeneity | 0.78 ± 0.06 (0.66, 0.88) | 54 (40/74) | 92 (12/13) |
| Tumor size | 0.81 ± 0.06 (0.68, 0.90) | 61 (45/74) | 92 (12/13) |
| | Differentiation between Grade 1-2 versus Grade 3 Tumors | | |
| RFISA | 0.77 ± 0.05 (0.65, 0.86) | 70 (16/23) | 77 (49/64) |
| Homogeneity | 0.70 ± 0.05 (0.59, 0.80) | 91 (21/23) | 47 (30/64) |
| Tumor size | 0.72 ± 0.05 (0.60, 0.81) | 52 (12/23) | 83 (53/64) |

TABLE 4

ROC Analysis of quantifiers in pairwise comparison of tumor grades. AUCs are cited with standard errors. Numbers in parentheses are 95% confidence intervals. Sensitivity and specificity are computed in terms of identification of the higher-grade tumors. Data in parentheses are numbers used to calculate percentages. The optimal cutoff values for differentiating between tumor grades were chosen at the highest possible sensitivity and specificity (maximal Youden index defined as sensitivity plus specificity minus 1) on the ROC curves.

| Quantifier | AUC | Sensitivity (%) | Specificity (%) |
|---|---|---|---|
| | Differentiation between Grade 1 versus Grade 2 Tumors | | |
| RFISA | 0.78 ± 0.08 (0.61, 0.90) | 76 (39/51) | 77 (10/13) |
| Homogeneity | 0.74 ± 0.07 (0.59, 0.85) | 49 (25/51) | 92 (12/13) |
| Tumor size | 0.77 ± 0.06 (0.63, 0.88) | 55 (28/51) | 92 (12/13) |
| | Differentiation between Grade 2 versus Grade 3 Tumors | | |
| RFISA | 0.74 ± 0.06 (0.61, 0.84) | 65 (15/23) | 78 (40/51) |
| Homogeneity | 0.68 ± 0.06 (0.55, 0.79) | 91 (21/23) | 41 (21/51) |
| Tumor size | 0.66 ± 0.06 (0.52, 0.79) | 52 (12/23) | 78 (40/51) |
| | Differentiation between Grade 1 versus Grade 3 Tumors | | |
| RFISA | 0.92 ± 0.05 (0.75, 0.98) | 96 (22/23) | 77 (10/13) |
| Homogeneity | 0.91 ± 0.05 (0.76, 0.98) | 96 (22/23) | 69 (9/13) |
| Tumor size | 0.89 ± 0.05 (0.75, 0.97) | 74 (17/23) | 92 (12/13) |

Traditionally, tumor grading has been performed by pathologists and requires preparation of sample slices and expert knowledge in tumor differentiation. We hypothesized that computerized image analysis methods can be useful for grading HCC tumors in pre-operative CT scans non-invasively. Our study reveals that the RFISA quantifier can be used as a pre-operative non-invasive marker of HCC tumor grades.

The RFISA quantifier extracts tumor characterizations from within an expert delineated tumor boundary. Compared to traditional histological analysis which focuses only on small parts of the biopsy sample, the RFISA quantifier captures holistic information from the whole tumor, thus reducing bias and sampling errors. Using the RFISA quantifier, we can characterize HCC into grade-1, grade-2, and grade-3, with accuracy as shown in Table 3 and Table 4. The calculation speed is less than one second on a typical personal computer. The differentiation of grade-1 vs. grade-3 has an AUC of 0.92±0.05, indicating that the RFISA quantifier can be used to distinguish between grade-1 and grade-3 samples. The grade-1 and grade-2 classification task has AUC 0.78±0.08, and the grade-2 vs. grade-3 classification task has AUC 0.74±0.06. The impact to patient care is that tumor grades can be obtained pre-operatively and non-invasively from CT images, which facilitates the decision making for therapy treatment strategy.

In addition to the RFISA quantifier, we investigated Homogeneity as a potential tumor grading marker. Homogeneity or heterogeneity are recognized features of lesions, reflecting areas of high cell density, necrosis, hemorrhage, and myxoid change. We investigated the complete set of 14 Haralick texture features, including Homogeneity, Energy, and Dissimilarity. Our results show that, among these 17 texture features, Homogeneity has the highest Spearman's rank correlation (denoted as R below) with tumor grade (R=−0.412, P<0.001), followed by Dissimilarity (R=0.410, P<0.001), Energy (R=−0.402, P<0.001), Entropy (R=0.401, P<0.001), and Contrast (R=0.364, P<0.001). However, its correlation with tumor grade is lower than RFISA (R=0.484, P<0.001). Also, its AUC is lower than RFISA in all categories in Table 3 and Table 4.

Regarding Tumor Size, we observed in the boxplot in FIG. 4 that tumors of higher grade tend to be larger in size. Additionally, the higher the tumor grade, the tendency of lower homogeneity and higher RFISA.

In FIG. 3, we illustrated that ISA image filters produce high responses on bar-like structures such as vessels within CT images, which implies that the RFISA quantifier captures vasculature.

It is to be understood that although the above-described training stage included a generally small number (84) of people, all collected from a single hospital, the patient population can be increased as well as hospital diversity. With a larger population, we could further stratify the patients based on tumor location and other factors. The data-driven ISA method could benefit from a larger dataset. By expanding the dataset, feature selection and validation can be performed on independent datasets instead of round-robin-by-case. The measurements discussed above were collected prior to therapy. It is to be understood that CT images can be collected before and after therapy, in order to use the RFISA quantifier for early therapy response prediction. Further, in the above discussion, only the arterial phase image is utilized. It is to be understood that venous phase images can be utilized and that quantifiers can be extracted from the combination of arterial and venous phase images.

In view of the above, the RFISA quantifier according to an exemplary embodiment of the present invention can act as a non-invasive, pre-operative, and fast (less than one second) tumor grade predictor based on CT imaging. The output from such quantitative image analysis may be useful in therapy planning and in the data mining of lesion characteristics, potentially contributing to personalized medicine.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article or manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 5:
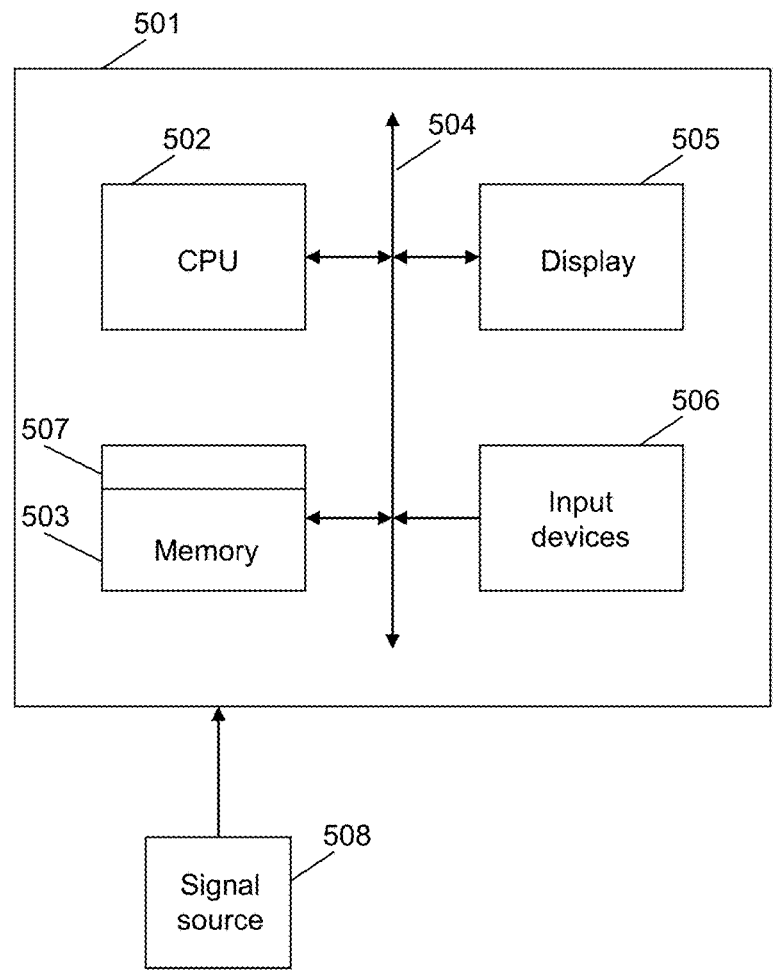
FIG. 5 is a computer system in which an exemplary embodiment of the present invention may be implemented.

Referring now to FIG. 5, according to an exemplary embodiment of the present invention, a computer system 501 can comprise, inter alia, a central processing unit (CPU) 502, a memory 503 and an input/output (I/O) interface 504. The computer system 501 is generally coupled through the I/O interface 504 to a display 505 and various input devices 506 such as a mouse and keyboard. The support circuits can include circuits such as cache, power supplies, clock circuits, and a communications bus. The memory 503 can include RAM, ROM, disk drive, tape drive, etc., or a combination thereof. Exemplary embodiments of present invention may be implemented as a routine 507 stored in memory 503 (e.g., a non-transitory computer-readable storage medium) and executed by the CPU 502 to process the signal from a signal source 508. As such, the computer system 501 is a general-purpose computer system that becomes a specific purpose computer system when executing the routine 507 of the present invention.

The computer system 501 also includes an operating system and micro-instruction code. The various processes and functions described herein may either be part of the micro-instruction code or part of the application program (or a combination thereof) which is executed via the operating system. In addition, various other peripheral devices may be connected to the computer system 501 such as an additional data storage device and a printing device.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described to best explain the principles of the invention and the practical application, and to enable others of ordinary skill in the art to understand the invention for various embodiments with various modifications as are suited to the particular use contemplated.

What is claimed is:

1. A method of determining the histological grade of Hepatocellular Carcinoma (HCC), comprising:
   acquiring a Computed Tomography (CT) image of a person including an HCC tumor;
   delineating the HCC tumor; and
   assigning a histological grade to the HCC tumor, wherein assigning the histological grade to the HCC tumor comprises:
   applying a plurality of filters to the HCC tumor, wherein each of the filters produces a corresponding response image and, for each of the filters, a convolution operation is performed on the filter and the CT image to produce the response image corresponding to that filter;
   computing an average response of the HCC tumor in each of the response images and recording each of the average responses as an Independent Subspace Analysis (ISA) feature; and
   determining the histological grade of the HCC tumor based on the ISA features by using a classifier.

2. The method of claim 1, wherein the classifier includes Random Forest regression.

3. The method of claim 1, wherein the histological grade of the HCC tumor includes grade-1, grade-2, or grade-3.

4. The method of claim 1, wherein the histological grade of the HCC tumor is obtained pre-operatively and non-invasively.

5. The method of claim 1, wherein the filters are obtained in a training stage.

6. The method of claim 5, wherein the training stage comprises:
   subjecting a plurality of sample CT images, each image having at least one HCC tumor delineated therein, to ISA to yield the plurality filters;
   applying the filters to each tumor by using the convolution operation;
   recording the average response per filter as an ISA feature; and
   using the classifier to predict the histological grade of each tumor based on its ISA features.

7. The method of claim 1, wherein the HCC tumor is delineated by a medical professional.

8. A system for determining the histological grade of Hepatocellular Carcinoma (HCC), comprising:
   a memory device for storing a program;
   a processor in communication with the memory device, the processor operative with the program to:
   acquire a Computed Tomography (CT) image of a person including an HCC tumor;
   delineate the HCC tumor; and
   assign a histological grade to the HCC tumor, wherein the processor is further operative with the program in assigning the histological grade to the HCC tumor to:
   apply a plurality of filters to the HCC tumor, wherein each of the filters produces a corresponding response image and, for each of the filters, a convolution operation is performed on the filter and the CT image to produce the response image corresponding to that filter;
   compute an average response of the HCC tumor in each of the response images and record each of the average responses as an Independent Subspace Analysis (ISA) feature; and
   determine the histological grade of the HCC tumor based on the ISA features by using a classifier.

9. The system of claim 8, wherein the classifier includes Random Forest regression.

10. The system of claim 8, wherein the histological grade of the HCC tumor includes grade-1, grade-2, or grade-3.

11. The system of claim 8, wherein the histological grade of the HCC tumor is obtained pre-operatively and non-invasively.

12. The system of claim 8, wherein the filters are obtained in a training stage.

13. The system of claim 12, wherein the processor is further operative with the program in the training stage to:
   subject a plurality of sample CT images, each image have at least one HCC tumor delineated therein, to ISA to yield the plurality filters;
   apply the filters to each tumor by using the convolution operation;
   record the average response per filter as an ISA feature; and use the classifier to predict the histological grade of each tumor based on its ISA features.

14. The system of claim 8, wherein the HCC tumor is delineated by a medical professional.

15. A computer program product for determining the histological grade of Hepatocellular Carcinoma (HCC), comprising:
a non-transitory computer readable storage medium having computer readable program code embodied therewith, the computer readable program code comprising:
computer readable program code configured to perform the steps of:
acquiring a Computed Tomography (CT) image of a person including an HCC tumor;
delineating the HCC tumor; and
assigning a histological grade to the HCC tumor, wherein assigning the histological grade to the HCC tumor comprises:
applying a plurality of filters to the HCC tumor, wherein each of the filters produces a corresponding response image and, for each of the filters, a convolution operation is performed on the filter and the CT image to produce the response image corresponding to that filter;
computing an average response of the HCC tumor in each of the response images and recording each of the average responses as an Independent Subspace Analysis (ISA) feature; and
determining the histological grade of the HCC tumor based on the ISA features by using a classifier.

16. The computer program product of claim 15, wherein the classifier includes Random Forest regression.

17. The computer program product of claim 15, wherein the histological grade of the HCC tumor includes grade-1, grade-2, or grade-3.

18. The computer program product of claim 15, wherein the histological grade of the HCC tumor is obtained pre-operatively and non-invasively.

19. The computer program product of claim 15, wherein the filters are obtained in a training stage.

20. The computer program product of claim 19, wherein the training stage comprises:
subjecting a plurality of sample CT images, each image having at least one HCC tumor delineated therein, to ISA to yield the plurality filters;
applying the filters to each tumor by using the convolution operation;
recording the average response per filter as an ISA feature; and
using the classifier to predict the histological grade of each tumor based on its ISA features.

21. The computer program product of claim 15, wherein the HCC tumor is delineated by a medical professional.

* * * * *